United States Patent [19]

Transue et al.

[11] Patent Number: 5,234,106
[45] Date of Patent: Aug. 10, 1993

[54] PACKAGE RETAINER FOR STERILE INSTRUMENTS

[75] Inventors: Deborah M. Transue, Bridgwater; Teresa M. Simons, Milltown, both of N.J.

[73] Assignee: Ethicon, Inc., Somerville, N.J.

[21] Appl. No.: 897,136

[22] Filed: Jun. 11, 1992

[51] Int. Cl.⁵ ...................... B65D 85/00; B65D 73/00
[52] U.S. Cl. .................... 206/363; 206/349; 206/438; 206/482; 206/483
[58] Field of Search ............... 206/363, 364, 349, 438, 206/439, 476, 477, 478, 481, 482, 483

[56] References Cited

U.S. PATENT DOCUMENTS

| 1,524,170 | 1/1925 | Carson | 206/482 |
| 1,913,105 | 6/1933 | Case et al. | 206/482 X |
| 2,224,027 | 12/1940 | Tate | 206/476 |
| 3,372,798 | 3/1968 | Thomas | 206/364 X |
| 4,023,678 | 5/1977 | Fiedler | 206/363 |
| 4,142,632 | 3/1979 | Sandel | 206/363 |
| 4,332,322 | 6/1982 | Jaeschke et al. | 206/364 |
| 4,506,787 | 3/1985 | Bruso | 206/363 |
| 4,512,466 | 4/1985 | Delang | 206/482 X |
| 4,597,493 | 7/1986 | Bruso | 206/363 |
| 4,711,352 | 12/1987 | Williams et al. | 206/481 X |
| 5,131,537 | 7/1992 | Gonzales | 206/364 |

Primary Examiner—Bryon P. Gehman

[57] ABSTRACT

A package retainer used to package sterile instruments. The package retainer has a plurality of cutout portions which engage the instrument to stabilize and suspend the instrument in the package.

4 Claims, 4 Drawing Sheets

PACKAGE RETAINER FOR STERILE INSTRUMENTS

FIELD OF INVENTION

This invention relates to a package retainer used for packaging sterile surgical instruments to aid in stabilizing the instrument within the package.

BACKGROUND OF THE INVENTION

Surgical instruments are becoming more widely used in surgical procedures. This is especially true with the advent of endoscopic or least invasive surgery. Many of these instruments are quite bulky in nature and have some weight to them. Because of this bulk and weight, the instruments are more difficult to package in a sterile manner than lightweight small needles, sutures and similar devices. One accepted method used for packaging these bulky, relatively heavy instruments is in thermoformed plastic blister packages. Often, these packages comprise a thermoformed plastic tray with a paper or film cover. Such thermoformed packages are bulky and difficult to dispose of causing considerable environmental concern. In packaging surgical products, it is often desirable to use heat sealed packages. Generally these packages comprise two layers of either film, paper, non-woven fabric or combinations of the same. The layers are heat-sealed together about their peripheries with any of the standard thermoplastic heat-sealable resins with the sterile item disposed between the layers. These heat sealable packages have become quite accepted because they're inexpensive and easy to open within the sterile environment. Furthermore, these type packages cause less environmental concern than the thermoformed plastic trays.

One of the problems that arises when packaging the bulky and relatively heavy sterile surgical instruments in a heat sealable and pealable package is that often during transportation of the instrument package or other handling of the instrument package prior to use, the instrument will move within the package and disrupt the heat seal and hence compromise the sterility of the instrument.

It is an object of the present invention to overcome these problems. It is an object of the present invention to stabilize a relatively bulky and heavy sterile instrument within a package. It is a further object of the present invention to assist in insuring that in a heat sealed package the heat seal is not compromised during the transportation or storage of the instrument package prior to use of the instrument. A still further object of the present invention is to provide a package that causes a minimum of environmental concern.

SUMMARY OF THE PRESENT INVENTION

What we have discovered is a new and improved package retainer for use in the packaging of relatively heavy, bulky sterile surgical instruments, especially in heat sealed packages.

In accordance with the present invention, the package retainer comprises a thin, relatively stiff member. This member has a length at least that of the instrument being packaged and a width at least that of the widest part of the instrument being packaged. The member includes a first cut-out portion which is folded back on itself to form a strap. One end of the strap is attached to the member while the other end of the strap, which is free, extends over a portion of the instrument and is releasably attached to the member. The member also includes a second cut-out portion. The second cut-out portion extends out of the plane of the member and, preferably, substantially perpendicular to the member. The second portion also engages the instrument to be packaged to stabilize the instrument within the package. In a preferred embodiment of the present invention, the second portion extends into an opening in the instrument, such as the handle of the instrument, to stabilize the instrument in position on the package insert.

The present invention further provides a new and improved package comprising a retainer as described above with an instrument suspended on the retainer and held in place. The retainer and instrument are disposed between an upper or top layer and a lower or bottom layer. The top layer is preferably transparent. At least one of the layers has a thermoplastic heat sealable resin disposed around at least three sides of the periphery of the layer. Also, thermoplastic heat sealable resin is disposed at the fourth side of said layer but inwardly of the edge of the layer. The top and bottom layers are heat sealed together at all four sides to provide a heat sealed package wherein at one edge of said package the layers are free of each other to provide an area of each layer that may be gripped in order to pull the layers apart and expose the instrument.

DETAILED DESCRIPTION OF THE DRAWINGS

Figure 1:
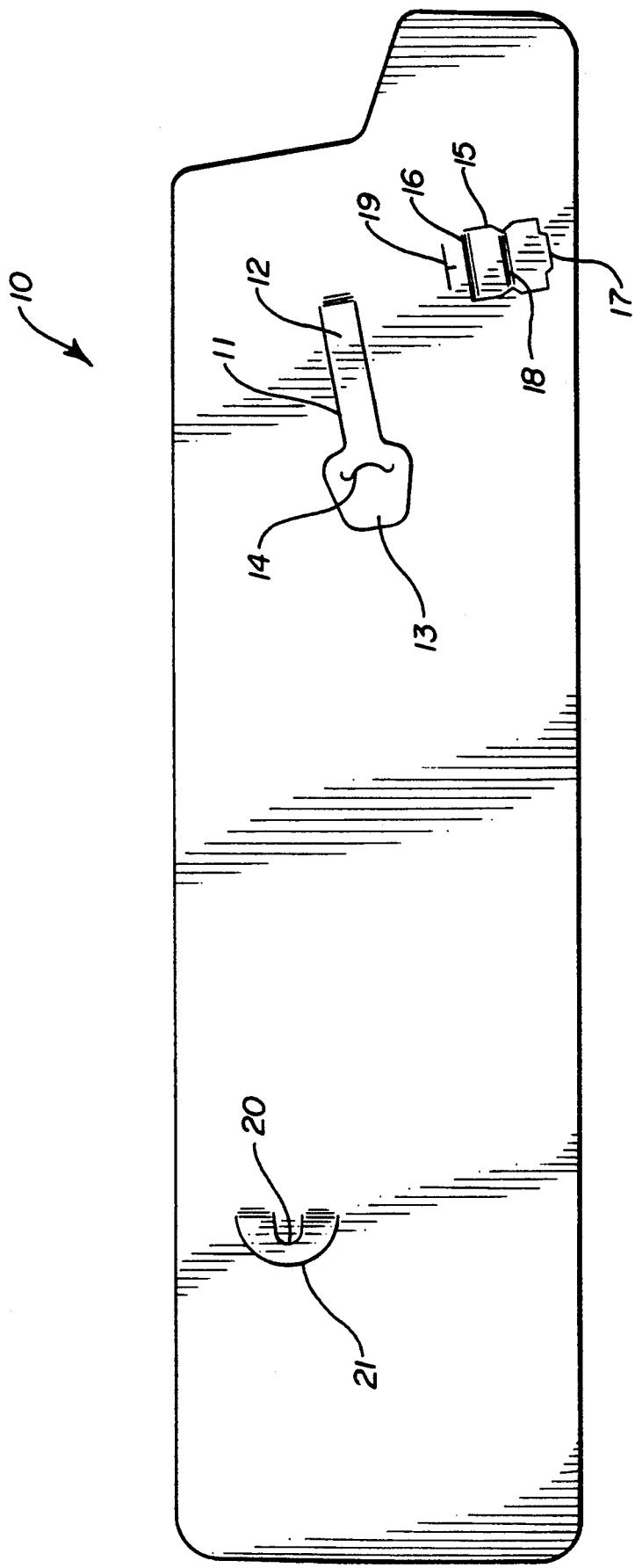
FIG. 1 is a plan view of the package insert of the present invention.

Referring to the drawings, in FIG. 1 there is shown a plan view of a preferred embodiment of the package retainer of the present invention. In this embodiment, the retainer comprises a thin, relatively stiff member 10. This member may be made from heavy paper, cardboard, or similar materials. A specific material that may be used to make the package retainer is 12 pt to 20 pt solid bleached sulfate board. As is seen, the package retainer is generally rectangular in shape. At one end there is a cutout of a strap 11. The strap has a relatively narrow band section 12, one end of which remains attached to the package retainer member and the other end is expanded into a square or round shape 13. In the expanded area, a slit 14 is disposed. Disposed below this strap cutout is a second cutout 15. This second cutout has a generally rectangular shape with one end 16 remaining attached to the package retainer member and the opposite end having an outwardly extending tab 17. In the center of this cutout portion is a foldline 18. For easy reference, this cutout will be called the "island cutout". Adjacent the portion where the island cutout remains attached to the member, there is also a slit 19 disposed in the package retainer member.

In this embodiment of the package retainer, a third cutout is also disposed in the package retainer member. This third cutout comprises substantially concentric semi-circular slits 20 and 21 wherein the portion of the cutout extending between the semi-circular slits remains attached to the package retainer member. For easy reference, this cutout will be referred to as the "semi-circular cutout".

Figure 2:
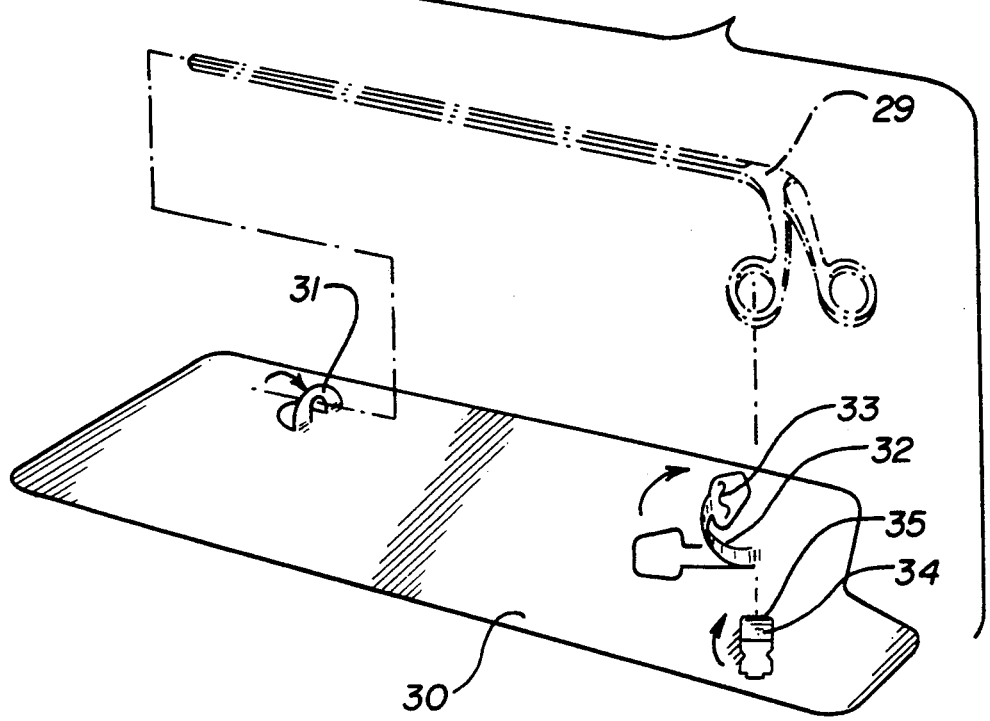
FIG. 2 is a perspective view of a package insert of the present invention depicting how an instrument is placed on the package.
Figure 3:
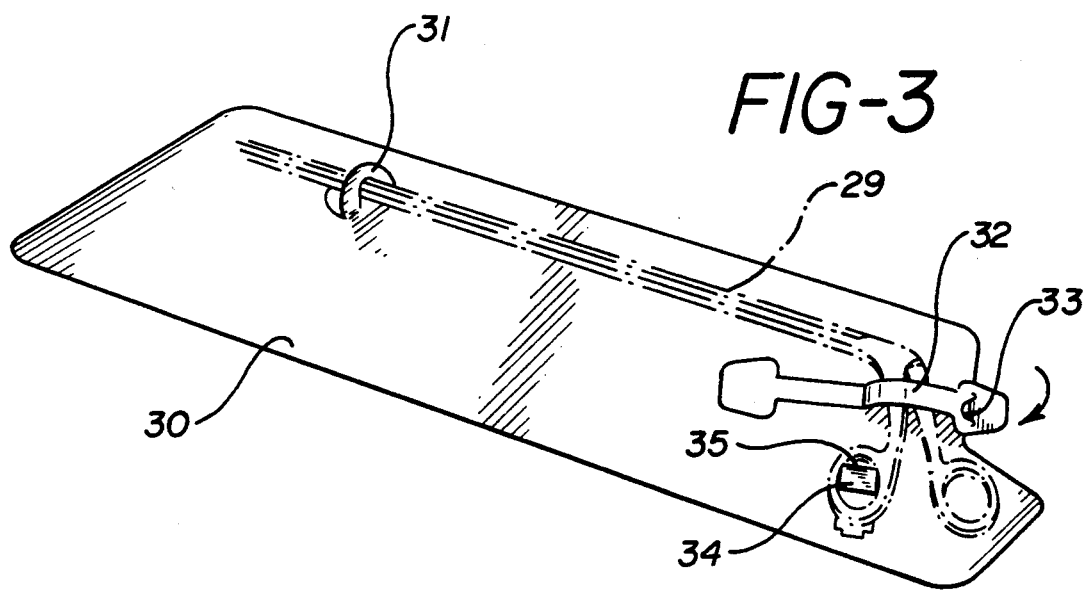
FIG. 3 is a perspective view of the package insert of FIG. 2 with an instrument disposed on the package insert.
Figure 4:
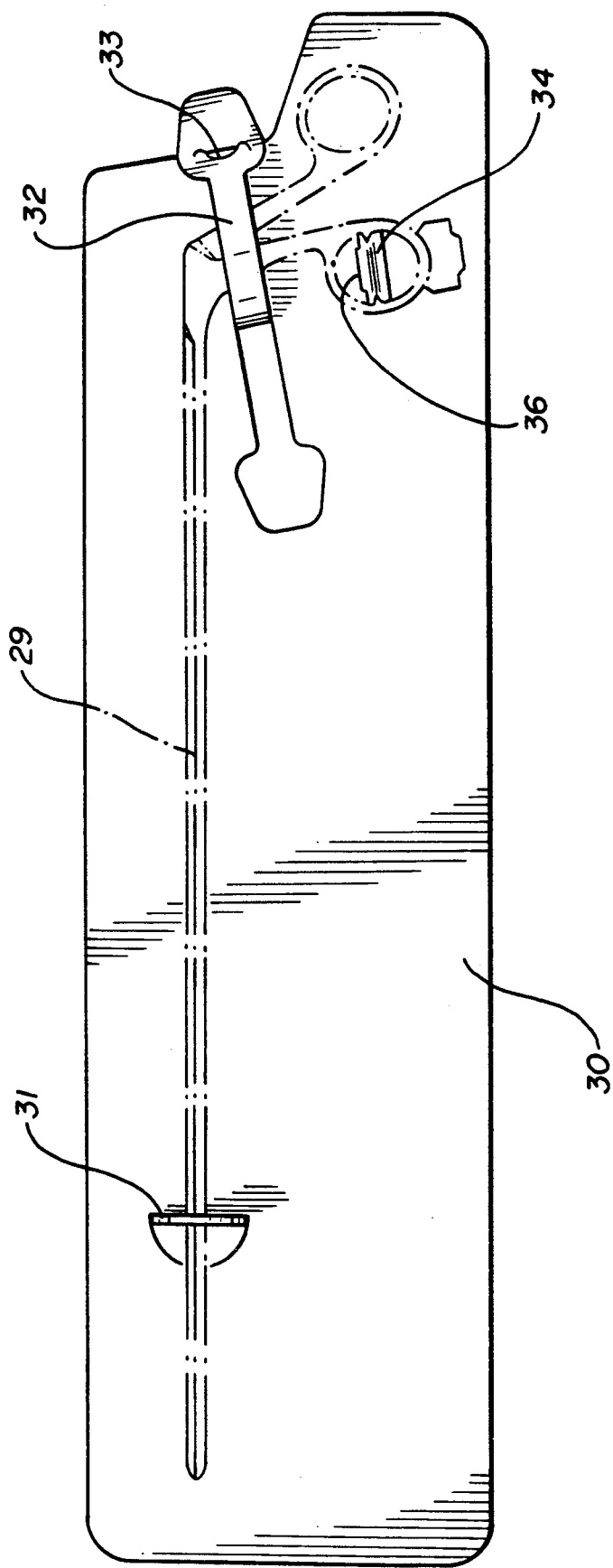
FIG. 4 is a plan view of a package insert of the present invention with an instrument depicted in place on the package insert.

The function of the cutouts and the manner in which an instrument is suspended on this package retainer will be more fully described in conjunction with FIGS. 2, 3, and 4.

Referring to the Figures, a suitable surgical instrument 29 such as a grasper, tissue manipulator, clip applier, etc. is placed on the package retainer 30. The package retainer has a length at least as long as the instrument disposed on the retainer. Also, the package retainer has a width at least equal or greater than the width of the instrument at the instrument's widest part. The instrument comprises an elongated business end and a scissor-like handle with openings in that scissor-like handle as is well known in the art. The semi-circular cutout 31 of the package retainer is disposed out of the plane of the package insert and substantially perpendicular to the insert as shown in FIG. 2. The elongated portion or business portion end of the instrument is slipped through the opening in the semi-circular cut-out and then laid on the package insert as depicted in FIG. 3. The strap cutout 32 is folded back on itself about the handle portion of the instrument and the tongue-lock 33 in this strap cutout engages the edge of the package retainer to lock the strap and the instrument in place. To assist in preventing movement of the instrument on the package retainer, the island cutout 34 is folded upwardly, substantially perpendicular to the package retainer, and then folded back on itself along the fold line 35 with the tab of this island cutout then inserted into the slit 36 in the package retainer. This island cutout fits within the opening in the handle of the instrument to stabilize the suspended instrument on the package retainer.

Figure 5:
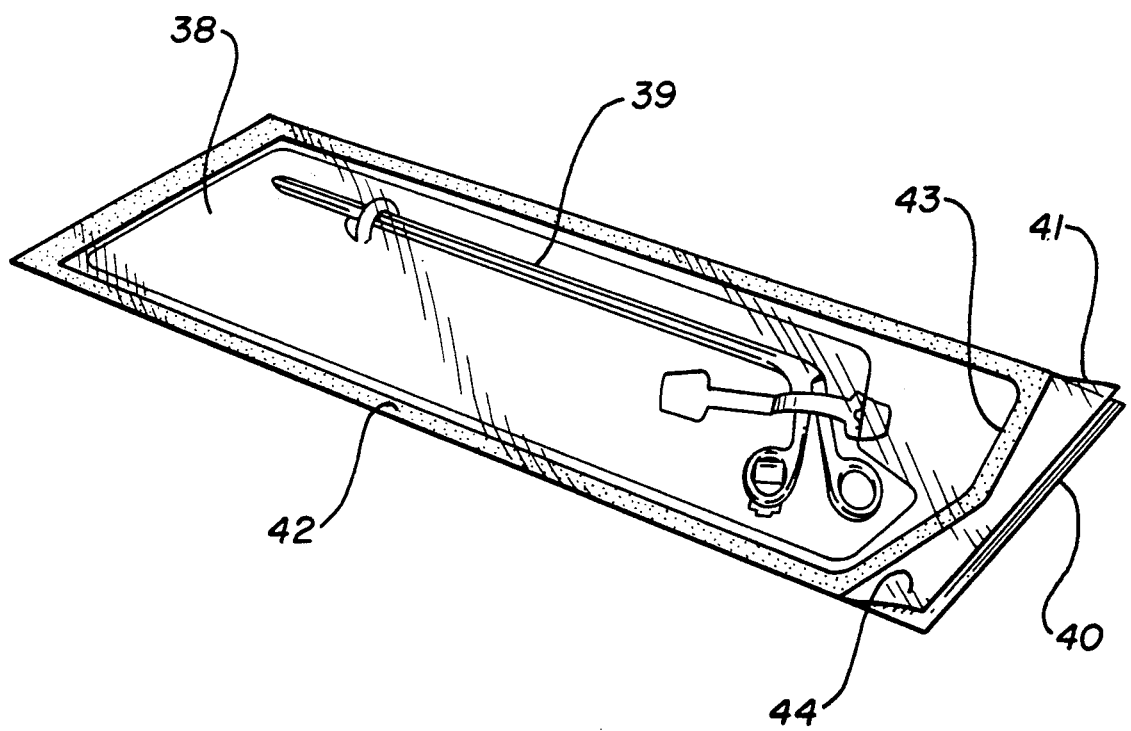
FIG. 5 is a perspective view showing the package insert of the present invention with an instrument placed on the insert and the insert and instrument disposed in a heat-sealed outerwrap.

As shown in FIG. 5, the package retainer 38 with the instrument 39 suspended thereon is placed in a heat-sealed package. The heat sealed package comprises a bottom layer 40 which may be paper, film, nonwoven fabric, or similar materials. A suitable bottom layer may be made from Tyvek TM non-woven material sold by duPont. The package includes an upper layer 41 or top layer. It is preferred that this upper layer be made of a clear or transparent film material, though other materials may be used. A suitable upper layer may be made from polypropylene copolymer film. A heat sealable resin 42 extends about the periphery of this layer at least on three sides thereof and is disposed inwardly from the periphery of the layer at one side thereof 43. Any of the well-known heat sealable resins may be used. The two layers are heat sealed together as is well known in the art. The portion of the upper layer and lower layer which extend outwardly from the inwardly disposed heat sealed section form the peelable portion 44. It is a simple matter for the user to grasp the two layers in the area where they are not heat sealed to peel back the upper layer and expose the sterile instrument.

Such packages may be sterilized by various of the sterilization techniques, such as radiation, ethylene oxide, etc. A preferred technique for stabilizing the package depicted in FIG. 5 is by cobalt irradiation.

The package retainer, as well as the heat sealable package itself, may be made from various plastic materials as well as films, papers, foils and various combinations of the same, depending on the type of instrument being packaged as well as the type of sterilization to be used. The selection of materials and combinations of materials, as well as the method of sealing are well within the skill of one skilled in the art of packaging such sterilizable surgical products.

Having now described the present invention, it will be understood by those skilled in the art that variations and modifications of the specific embodiments described above may be employed without departing from the spirit and scope of the present invention as defined in the appended claims.

What is claimed is:

1. A package retainer for use in the sterile packaging of a surgical instrument, said retainer comprising a thin, stiff member having a length at least that of the instrument to be packaged and a width at least that of the instrument to be packaged at said instrument's widest point, said member having a first cutout portion folded back on itself to form a strap, one end of said strap remaining attached to said member and the other end of said strap being a free end whereby said strap may extend over a portion of the instrument to be packaged with its free end releasably attached to said member to stabilize said instrument, said member including a second cutout portion, said cutout portion being substantially rectangular in shape with one end attached to said member and a tab at the edge opposite said attached end, said second cutout portion being foldable about a center line to allow said tab to be inserted into a slit in said member, and said second cutout portion extending out of the plane of said member to engage the instrument to be packaged, said member further including a third cutout portion extending out of the plane of said member, said third portion being substantially semicircular in shape with an opening in said third portion, said third portion being attached to said member and said opening being disposed to engage a portion of the instrument to be packaged.

2. A sterile surgical instrument package comprising a thin, stiff member of substantially rectangular shape and having a length at least that of the instrument packaged and a width at least that of the instrument packaged at said instrument's widest point, said member having a first cutout portion folded back on itself to form a strap, one end of said strap remaining attached to said member and the other end of said strap being a free end, said strap extending over a portion of the instrument with its free end releasably attached to said member to stabilize said instrument, said member including a second cutout portion, said second cutout portion being substantially rectangular in shape with one end attached to said member and a tab at the end opposite said attached end, said second cutout portion being foldable about a center line to allow said tab to be inserted into a slit in said member, and said second cutout portion extending out of the plane of said member and engaging the instrument said member further including a third cutout portion extending out of the plane of said member, said third portion being substantially semi-circular in shape with an opening in said third portion, said third portion being attached to said member and said opening engaging a portion of the instrument packaged, a bottom layer disposed on one side of said member and extending beyond all edges of said member, a top layer disposed on the other side of said member, said top layer and said bottom layer being co-extensive, a heat sealed resin disposed on one of said layers and extending beyond all edges of said member.

3. A package according to claim 2 wherein the top layer is made from transparent material.

4. A package according to claim 2 wherein the top and bottom layers extend beyond the heat seal at one side of said package to provide an unsealed portion on each layer to assist in separation of the heat sealed layers.

* * * * *